(12) United States Patent
Rapta et al.

(10) Patent No.: US 10,640,467 B2
(45) Date of Patent: May 5, 2020

(54) PROCESS FOR PREPARING 2-(1-(TERT-BUTOXYCARBONYL)PIPERIDINE-4-YL)BENZOIC ACID

(71) Applicant: THERAVANCE BIOPHARMA R&D IP, LLC, South San Francisco, CA (US)

(72) Inventors: Miroslav Rapta, San Carlos, CA (US); Dimitar Filipov, San Francisco, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

(21) Appl. No.: 16/425,166

(22) Filed: May 29, 2019

(65) Prior Publication Data

US 2019/0367455 A1  Dec. 5, 2019

Related U.S. Application Data

(60) Provisional application No. 62/679,586, filed on Jun. 1, 2018.

(51) Int. Cl.
*C07D 211/34* (2006.01)

(52) U.S. Cl.
CPC .................. *C07D 211/34* (2013.01)

(58) Field of Classification Search
CPC .................................................. C07D 211/34
USPC ........................................................ 546/226
See application file for complete search history.

(56) References Cited

U.S. PATENT DOCUMENTS

| | | | |
|---|---|---|---|
| 2,891,066 A | 6/1959 | Parcell et al. | |
| 8,247,433 B2 | 8/2012 | Stangeland et al. | |
| 8,304,432 B2 | 11/2012 | Patterson et al. | |
| 8,304,433 B2 | 11/2012 | Patterson et al. | |
| 8,592,596 B2 | 11/2013 | Patterson et al. | |
| 8,604,058 B2 | 12/2013 | Patterson et al. | |
| 8,802,857 B2 | 8/2014 | Stangeland et al. | |
| 9,073,859 B2 | 7/2015 | Patterson et al. | |
| 9,162,982 B2 | 10/2015 | Patterson et al. | |
| 9,187,423 B2 | 11/2015 | Stangeland et al. | |
| 9,675,599 B2 | 6/2017 | Patterson et al. | |
| 10,034,870 B2 | 7/2018 | Patterson et al. | |
| 10,206,913 B2 | 2/2019 | Patterson et al. | |
| 10,226,454 B2 | 3/2019 | Patterson et al. | |
| 10,238,642 B2 | 3/2019 | Hegde | |

OTHER PUBLICATIONS

Kozaka et al., "Syntheses and in vitro evaluation of decalinvesamicol analogues as potential imaging probes for vesicular acetylcholine transporter (VAChT)", Bioorganic & Medicinal Chemistry, 20: 4936-4941 (2012).
International Search Report and Written Opinion for PCT/US2019/034332 dated Aug. 16, 2019.
Reaxys_XP002793273_2010.
XP002793274_Dec. 21, 2009.
Tang et al., "Design and synthesis of a new class of malonyl-CoA decarboxylase inhibitors with anti-obesity and anti-diabetic activities", Bioorganic & Medicinal Chemistry Letters, 20: 6088-6092 (2010).

*Primary Examiner* — Taofiq A Solola
(74) *Attorney, Agent, or Firm* — Jeffrey A. Hagenah

(57) ABSTRACT

The invention relates to processes for preparing 2-(1-(tert-butoxycarbonyl)-piperidine-4-yl)benzoic acid having formula I:

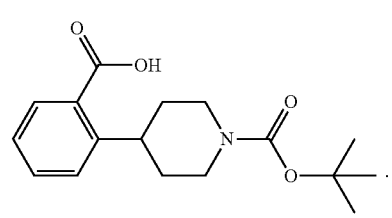

Among its various uses, this compound is useful as an intermediate for preparing ampreloxetine and salts thereof.

17 Claims, No Drawings

PROCESS FOR PREPARING 2-(1-(TERT-BUTOXYCARBONYL)PIPERIDINE-4-YL) BENZOIC ACID

CROSS-REFERENCE TO RELATED APPLICATIONS

This application claims the benefit of U.S. Provisional Application No. 62/679,586, filed on Jun. 1, 2018; the entire disclosure of which is incorporated herein by reference in its entirety.

BACKGROUND OF THE INVENTION

Field of the Invention

The present invention relates to processes for preparing 2-(1-(tert-butoxycarbonyl)piperidine-4-yl)benzoic acid.

State of the Art

Ampreloxetine is a norepinephrine reuptake inhibitor having the formula:

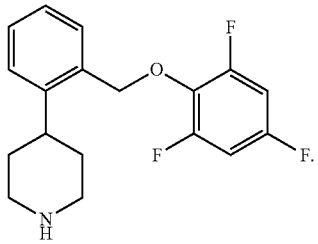 [SMILES: Fc1cc(F)c(OCc2ccccc2C2CCNCC2)c(F)c1]

Ampreloxetine is also known as TD-9855 or 4-[2-(2,4,6-trifluorophenoxymethyl)phenyl]-piperidine and is disclosed in U.S. Pat. Nos. 8,304,432; 8,604,058; 9,162,982; 9,675,599; 10,034,870; and 10,206,913. Additionally, U.S. Pat. Nos. 8,304,433; 8,592,596; and 9,073,859 disclose a crystalline hydrochloride salt of ampreloxetine; and U.S. Pat. No. 10,238,642 discloses methods for treating neurogenic orthostatic hypotension using ampreloxetine or a pharmaceutically-acceptable salt thereof.

These patents disclose that ampreloxetine and salts thereof can be prepared using 2-(1-(tert-butoxycarbonyl) piperidine-4-yl)benzoic acid (also known as 4-(2-carboxyphenyl)piperidine-1-carboxylic acid t-butyl ester) as a process intermediate. This intermediate compound has formula I:

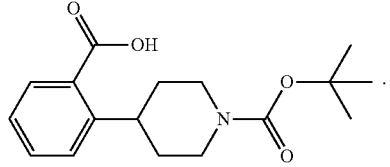

Accordingly, a need exists for new efficient processes for preparing 2-(1-(tert-butoxycarbonyl)piperidine-4-yl)benzoic acid (I).

SUMMARY OF THE INVENTION

The present invention relates to novel processes for preparing 2-(1-(tert-butoxycarbonyl)piperidine-4-yl)benzoic acid (I). Among its various uses, this compound is useful as an intermediate for preparing ampreloxetine and salts thereof.

Accordingly, in one aspect, the present invention provides a process for preparing a compound of formula I:

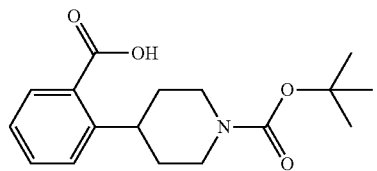

the process comprising:
(a) reacting a compound of formula 1:

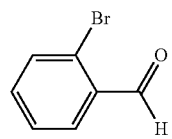

with a $C_{1-6}$ alkyl 3-oxobutanoate in the presence of piperidine to form a compound of formula 2:

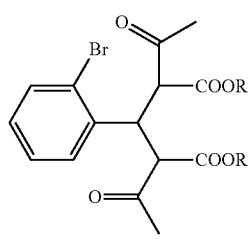

wherein each R is independently selected from $C_{1-6}$ alkyl;
(b) reacting the compound of formula 2 with an alkali metal hydroxide to form, after acidification of the reaction product with an acid, a compound of formula 3:

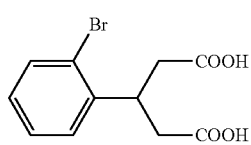

(c) reacting the compound of formula 3 with an ammonia reagent to form a compound of formula 4:

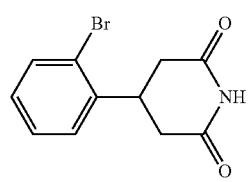

(d) reacting the compound of formula 4 with a reducing agent to form a compound of formula 5 or a salt thereof:

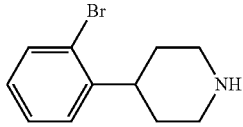

(e) reacting the compound of formula 5 or a salt thereof with di-tert-butyl dicarbonate to form a compound of formula 6:

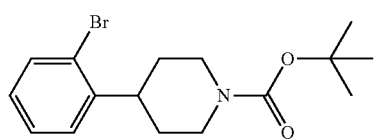

(f) reacting the compound of formula 6 with an alkyl lithium reagent to form a compound of formula 7:

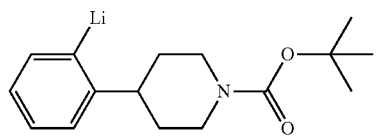

(g) reacting the compound of formula 7 with carbon dioxide to form the compound of formula I.

In one embodiment of the process, each R group is independently methyl or ethyl.

In another embodiment, both R groups are methyl. In another embodiment, both R groups are ethyl.

In one embodiment of the process, the alkali metal hydroxide is lithium hydroxide, sodium hydroxide or potassium hydroxide. In a particular embodiment, the alkali metal hydroxide is potassium hydroxide.

In one embodiment of the process, the acid is hydrochloric acid, hydrobromic acid, sulfuric acid, phosphoric acid or acetic acid. In a particular embodiment, the acid is hydrochloric acid.

In one embodiment of the process, the ammonia reagent is ammonia, urea, ammonium hydroxide, ammonium chloride or magnesium nitride. In a particular embodiment, the ammonia reagent is urea.

In one embodiment of the process, the reducing agent is sodium borohydride/boron trifluoride tetrahydrofuran complex or lithium aluminum hydride. In a particular embodiment, the reducing agent is sodium borohydride/boron trifluoride tetrahydrofuran complex.

In one embodiment of the process, alkyl lithium reagent is n-butyl lithium or tert-butyl lithium. In a particular embodiment, the alkyl lithium reagent is n-butyl lithium.

In one embodiment of the process, the alkali metal hydroxide is potassium hydroxide; the acid is hydrochloric acid; the reducing agent is sodium borohydride/boron trifluoride tetrahydrofuran complex; and the alkyl lithium reagent is n-butyl lithium.

In another aspect, the present invention relates to a process for preparing a compound of formula I:

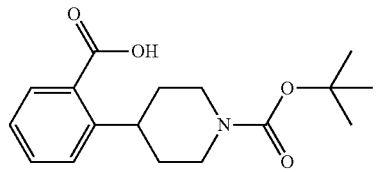

the process comprising:

(a) reacting a compound of formula 1:

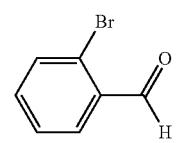

with ethyl 3-oxobutanoate in the presence of piperidine to form a compound of formula 2a:

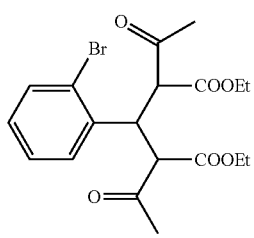

(b) reacting the compound of formula 2a with an potassium hydroxide to form, after acidification of the reaction product with hydrochloric acid, a compound of formula 3:

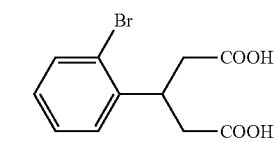

(c) reacting the compound of formula 3 with urea to form a compound of formula 4:

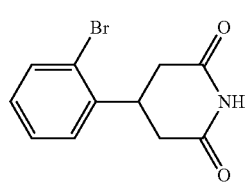

(d) reacting the compound of formula 4 with sodium borohydride/boron trifluoride tetrahydrofuran complex to form a compound of formula 5 or a salt thereof:

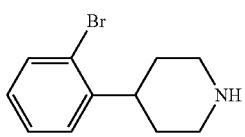

(e) reacting the compound of formula 5 or a salt thereof with di-tert-butyl dicarbonate to form a compound of formula 6:

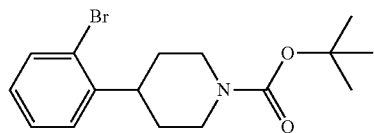

(f) reacting the compound of formula 6 with n-butyl lithium to form a compound of formula 7:

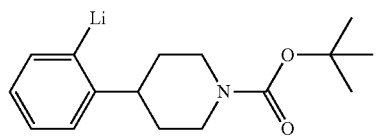

(g) reacting the compound of formula 7 with carbon dioxide to form the compound of formula I.

In one embodiment, step (d) and step (e) are conducted in the same reaction mixture without isolation of the product from step (d) thereby generating less waste and improving the overall efficiency and yield of the process.

Other aspects and embodiments of this invention are disclosed herein.

DETAILED DESCRIPTION OF THE INVENTION

In its various aspects and embodiments, the present invention relates to processes for preparing 2-(1-(tert-butoxycarbonyl)piperidine-4-yl)benzoic acid (I).

Definitions

When describing present invention, the following terms have the following meanings unless otherwise indicated.

The singular terms "a," "an" and "the" include the corresponding plural terms unless the context of use clearly dictates otherwise.

The term "about" means±5 percent of the specified value.

The term "alkyl" means a monovalent saturated hydrocarbon group which may be linear or branched. Unless otherwise defined, such alkyl groups typically contain from 1 to 6 carbon atoms. Representative alkyl groups include, by way of example, methyl, ethyl, n-propyl, isopropyl, n-butyl, sec-butyl, isobutyl, tert-butyl, n-pentyl, n-hexyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "pharmaceutically-acceptable" means acceptable for administration to a patient (e.g., having acceptable safety for the specified usage).

The term "pharmaceutically-acceptable salt" means a salt prepared from an acid and a base (including zwitterions) that is acceptable for administration to a patient (e.g., a salt having acceptable safety for a given dosage regime).

All other terms used herein are intended to have their ordinary meaning as understood by persons having ordinary skill in the art to which they pertain.

Process Conditions

The present invention relates to processes for preparing 2-(1-(tert-butoxycarbonyl)piperidine-4-yl)benzoic acid (I).

In the first step of the process, 2-bromobenzaldehyde (1) is reacted with about 2 to about 3 molar equivalents of $C_{1-6}$ alkyl 3-oxobutanoate, such as methyl 3-oxobutanoate or ethyl 3-oxobutanoate, in the presence of about 0.2 to about 0.4 molar equivalents of piperidine to form a di-$C_{1-6}$ alkyl 2,4-diacetyl-3-(2-bromophenyl)pentanedioate (2). The starting materials for this reaction are commercially available or can be prepared from commercially available materials using conventional procedures. This reaction is typically conducted in a diluent, such as methanol, ethanol and the like (typically, the alcohol corresponding to the alkyl group of the alkyl 3-oxobutanoate is employed as the diluent). The piperidine is typically added slowly to a mixture of the 2-bromobenzaldehyde and the alkyl 3-oxobutanoate in the diluent at a temperature ranging from about −20° C. to about 20° C. The resulting solution is then typically heated to reflux, e.g. a temperature in the range of from about 50° C. to about 100° C., for about 1 to about 6 hours or until the reaction is substantially complete. Upon completion of the reaction, the product can be isolated using conventional procedures, such as filtration, chromatography, recrystallization, and the like. Alternatively, the reaction mixture can be used directly in the next step of the process.

The di-$C_{1-6}$ alkyl 2,4-diacetyl-3-(2-bromophenyl)pentanedioate (2) is then reacted with an excess of an alkali metal hydroxide, such as lithium hydroxide, sodium hydroxide or potassium hydroxide, to form, after acidification of the reaction product with an acid, 3-(2-bromophenyl)pentanedioic acid (3). An aqueous solution of the alkali metal hydroxide is typically added slowly to the di-$C_{1-6}$ alkyl 2,4-diacetyl-3-(2-bromophenyl)pentanedioate (2) in a diluent, such as such as methanol, ethanol and the like, at a temperature ranging from about 50° C. to about 100° C. The resulting reaction mixture is then typically heated at a temperature in the range of from about 50° C. to about 100° C., for about 1 to about 6 hours or until the reaction is substantially complete. The reaction mixture is then acidified to pH 1-2 with an acid. Any suitable acid can be used in this reaction including, but not limited to, hydrochloric acid, hydrobromic acid, sulfuric acid, phosphoric acid, acetic acid and the like. Upon completion of the reaction, the product is isolated using conventional procedures, such as filtration, chromatography, recrystallization, and the like.

In the next step of the process, 3-(2-bromophenyl)pentanedioic acid (3) is reacted with an ammonia reagent, i.e., a reagent that generates ammonia. Any suitable ammonia reagent can be used including, but not limited to, ammonia, urea, ammonium hydroxide, ammonium chloride, magnesium nitride and the like. In one embodiment, the ammonia reagent is urea. In this embodiment, 3-(2-bromophenyl) pentanedioic acid (3) is reacted with about 1 to about 1.1 molar equivalents of urea to form 4-(2-bromophenyl)piperidine-2,6-dione (4). This reaction is typically conducted at a temperature in the range of from about 180° C. to about 210° C., for about 2 to about 10 hours or until the reaction is substantially complete. Upon completion of the reaction, the product is isolated using conventional procedures, such as filtration, chromatography, recrystallization, and the like.

4-(2-Bromophenyl)piperidine-2,6-dione (4) is then contacted with a reducing agent to form 4-(2-bromophenyl) piperidine (5). Any suitable reducing agent can be employed in this reaction including, but not limited to, sodium borohydride/boron trifluoride tetrahydrofuran complex, lithium aluminum hydride and the like. In this reaction, 4-(2-bromophenyl)piperidine-2,6-dione (4) is typically added slowly to a molar excess of the reducing agent and a suitable diluent, such as THF and the like, at a temperature in the range of from about −20° C. to about 0° C. When the addition is complete, the resulting mixture is generally heated at a temperature in the range of from about 40° C. to about 100° C. for about 2 to about 12 hours or until the reaction is substantially complete. Upon completion of the reaction, the product can be isolated using conventional procedures, such as filtration, chromatography, recrystallization, and the like. Alternatively, the reaction mixture can be used in the next step of the process.

In the next step of the process, 4-(2-bromophenyl)piperidine (5) is reacted with di-tert-butyl dicarbonate to form tert-butyl 4-(2-bromophenyl)piperidine-1-carboxylate (6). This reaction is typically conducted by contacting 4-(2-bromophenyl)piperidine (5) with about 1 molar equivalent of di-tert-butyl dicarbonate in a diluent, such as THF or THF/water and the like. Typically, this reaction is conducted in the presence of an alkali metal carbonate, such as sodium carbonate or potassium carbonate, or a sterically hindered organic amine, such as N,N-diisopropylethylamine and the like. This reaction is typically conducted at a temperature in the range of from about 10° C. to about 30° C., for about 1 to about 6 hours or until the reaction is substantially complete. Upon completion of the reaction, the product is isolated using conventional procedures, such as filtration, chromatography, recrystallization, and the like.

tert-Butyl 4-(2-bromophenyl)piperidine-1-carboxylate (6) is then reacted with an alkyl lithium reagent to form in situ (2-(1-(tert-butoxycarbonyl)piperidin-4-yl)phenyl)lithium (7) which is then reacted with carbon dioxide to form 2-(1-(tert-butoxycarbonyl)-piperidine-4-yl)benzoic acid (I). Any suitable alkyl lithium reagent can be used in this reaction including, but not limited to, is n-butyl lithium or tert-butyl lithium. This reaction is typically conducted in an anhydrous diluent, such as THF and the like, using about 1.1 to about 1.3 molar equivalents of the alkyl lithium reagent at a temperature in the range of from about −100° C. to about −60° C., for about 0.5 to about 3 hours or until the reaction is substantially complete. Excess dry ice is then added portionwise typically over a period of about 1 to about 4 hours and the resulting mixture stirred for about 6 to about 24 hours or until the reaction is substantially complete. Upon completion of the reaction, the product is isolated using conventional procedures, such as filtration, chromatography, recrystallization, and the like.

EXAMPLES

The following examples are provided to illustrate various representative embodiments and aspects of this invention and are not intended to limit the scope of this invention unless specifically indicated.

All reagents, starting materials and solvents used in the following examples were purchased from commercial suppliers (such as Sigma-Aldrich, St. Louis, Mo. and its affiliates) and were used without further purification unless otherwise indicated.

The following abbreviations have the following meanings unless otherwise indicated:
DCM dichloromethane
DMF N,N-dimethylformamide
DMSO dimethyl sulfoxide
EtOAc ethyl acetate
EtOH ethanol
IPA isopropyl alcohol
IPAc isopropyl acetate
MeCN acetonitrile
MeOH methanol
MTBE methyl tert-butyl ether
PET petroleum ether
TFA trifluoroacetic acid
THF tetrahydrofuran Other abbreviations used herein but not defined have their ordinary meaning as understood by persons having ordinary skill in the art to which they pertain.

$^1$H NMR spectra were recorded on a 300 MHz spectrometer, unless otherwise indicated. Chemical shifts are reported as δ values in ppm relative to tetramethylsilane (TMS) as an internal standard. Coupling constants (J values) are given in hertz (Hz) and multiplicities are reported using the following abbreviations: s=singlet, d=doublet, t=triplet, q=quartet, m=multiplet, br=broad, nd=not determined.

Example 1

Preparation of Diethyl 2,4-Diacetyl-3-(2-bromophenyl)pentanedioate (2a)

To a solution of ethyl 3-oxobutanoate (43.5 kg, 0.334 kmol) in ethanol (50 kg) was added 2-bromobenzaldehyde (1) (23 kg, 0.124 kmol) portionwise as a solid over a period of about 10 minutes. Piperidine (2.5 kg, 0.0294 kmol) was then added dropwise over a period of 10 minutes while maintaining the temperature at 8° C. to 11° C. The mixture was then heated to reflux and was refluxed for 3 hours. TLC (PET:EtOAc 5:1) showed no 2-bromobenzaldehyde remaining. The reaction mixture containing compound 2a was cooled to 30° C. to 50° C. and was used directly in the next step.

Example 2

Preparation of 3-(2-Bromophenyl)pentanedioic Acid (3)

To a solution of potassium hydroxide (115 kg, 2.05 kmol) in water (115 kg) at 75° C. to 85° C. was added the reaction mixture from Example 1 dropwise over a period of about 5 hours. After the addition was complete, the mixture was refluxed for about 8 hours. TLC (PET:EtOAc 1:1) indicated that compound 2a was no longer present. The mixture was cooled to 40° C. and concentrated under vacuum to remove ethanol. The residue was extracted with MTBE (50 kg). The pH of the aqueous layer was adjusted to pH 1-2 with concentrated hydrochloric acid (245 kg) keeping the temperature below 60° C. During the acidification, solid material precipitated out of solution. The mixture was cooled to 10° C. to 20° C. and stirred for 30 minutes. The mixture was then filtered and the filter cake was washed with water (2×50 kg) and MTBE (1×5 kg). The resulting solid was dried to afford compound 3 (33 kg, 0.115 kmol, 92.4% yield) as a light yellow solid.

Example 3

Preparation of 4-(2-Bromophenyl)piperidine-2,6-dione (4)

A blended mixture of 3-(2-bromophenyl)pentanedioic acid (3) (33 kg, 0.115 kmol) and urea (7.6 kg, 0.127 kmol) was stirred in an oil bath (bath temperature: 190° C. to 200° C.) for 6 hours. TLC (DCM:MeOH 10:1) indicated compound 3 was no longer present. The mixture was cooled to 100° C. and DMF (40 kg) was added carefully and then the mixture was cooled to room temperature with stirring. The mixture was filtered, the filter cake was washed with water (1×50 kg), ethanol (1×20 kg), and dried to afford compound 4 (20 kg, 0.075 kmol, 64.9% yield) as a white solid.

Example 4

Preparation of 4-(2-Bromophenyl)piperidine (5)

To THF (65 kg) was added sodium borohydride (5.7 kg, 0.151 kmol) portionwise under a dry nitrogen atmosphere. Boron trifluoride etherate (28 kg, 0.200 kmol) was then added dropwise at −10° C. to 0° C. over a period of 3 hours under nitrogen. The resulting mixture was stirred at −5° C. to 0° C. for 3 hours. 4-(2-Bromophenyl)piperidine-2,6-dione (4) (13 kg, 0.0485 kmol) was added portionwise under nitrogen at −10° C. to 0° C. over a period of 2 hours. The mixture was stirred at −5° C. to 0° C. for 3 hours and then heated slowly to 65° C. over period of 7 hours and then refluxed for 3 hours. TLC (DCM:MeOH 20:1) showed compound 4 was no longer present. The mixture was cooled to 20° C. to 30° C. and water (10 kg) was added dropwise over a period of 2.5 hours while keeping the temperature below 30° C. Aqueous 6 N hydrochloric acid (12 kg) was added dropwise over a period of 1 hour while keeping the temperature below 50° C. to adjust the pH to 1-2 and the mixture was heated to reflux for 4 hours and then cooled to 20° C. to 30° C. The reaction mixture was used directly in the next step.

Example 5

Preparation of tert-Butyl 4-(2-Bromophenyl)piperidine-1-carboxylate (6)

To the reaction mixture from Example 5 was added potassium carbonate (22 kg) to adjust the pH to 12-13. Di-tert-butyl dicarbonate (9.7 kg, 0.0444 kmol) was added portionwise over a period of 2 hours while maintaining the reaction temperature below 35° C. The resulting mixture was stirred at 25° C. to 35° C. for 2 hs. TLC (DCM:MeOH 10:1) showed compound 5 was no longer present. The mixture was concentrated under vacuum at 50° C. to remove THF. The residue was filtered and the filter cake was washed with MTBE (1×60 kg). The aqueous layer was separated and extracted with MTBE (1×40 kg, 1×20 kg). The combined organic layers were washed with brine (1×30 kg) and then sodium sulfate (5 kg), silica gel (600 mesh, 3 kg) and charcoal (4 kg) were added to the organic layer. This mixture was heated to reflux with stirring for 1 hour and then cooled to room temperature and filtered. The filtrate was concentrated to afford compound 6 (13.5 kg, 0.0397 kmol, 81.8% yield) as oil, which was used directly in the next step without further purification.

Example 6

Preparation of 2-(1-(tert-Butoxycarbonyl)piperidine-4-yl)benzoic Acid (I)

To a solution of tert-butyl 4-(2-bromophenyl)piperidine-1-carboxylate (6) (13.5 kg, 0.0397 kmol) in anhydrous THF (80 kg) was added dropwise n-butyl lithium (2.5 M in n-hexane, 13.75 kg, 0.0496 kmol) at −85° C. to −72° C. over a period of 1 hour under dry nitrogen. The resulting mixture was stirred at −75° C. to −70° C. for 2 hours. Dry ice (10 kg, 0.227 kmol) was added portionwise at −80° C. to −69° C. over a period of 2 hours under dry nitrogen. The mixture was warmed to −58° C. over a period of 12 hours. TLC (PET:EtOAc 10:1) indicated compound 6 was no longer present. Water (50 kg) was added dropwise while keeping the reaction temperature below 10° C. The mixture was then concentrated under vacuum at 35° C. to 45° C. to remove THF (~60 kg). The residue was adjusted to pH 10-11 with 10% aqueous sodium hydroxide (18.5 kg) while keeping the mixture temperature below 20° C. The mixture was extracted with MTBE (2×50 kg). The aqueous layer was acidified to pH 2-3 with aqueous 3 N hydrochloric acid (~40 kg) while keeping the mixture temperature below 10° C. Ethyl acetate (50 kg) was added and the mixture was stirred for 30 minutes. The aqueous layer was separated and extracted with ethyl acetate (2×30 kg). The combined organic layers were washed with an aqueous solution of sodium chloride (1×5 kg) in water (1×15 kg), dried with sodium sulfate (5 kg) and filtered. The filtrate was concentrated to a volume of about 40 L during which time, a precipitate formed. Petroleum ether (80 L) was added dropwise at 60° C. and the resulting mixture was allowed to cool to room temperature. The mixture was filtered to afford compound I (3.95 Kg). The filtrate was concentrated to obtain crude compound I (1.8 kg), which was crystallized from EtOAc (3.6 L) and PET (7.2 L) to afford the second crop of compound I (1.173 kg). The two crops were combined to afford compound I (5.123 kg, 0.0168 kmol, 34.5% yield) as a white solid.

$^1$H NMR (300 MHz, CDCl$_3$) δ (ppm) 8.00 (d, J=7.8 Hz, 1H); 7.55 (dd, J=0.9 and 7.8 Hz, 1H); 7.40 (d, J=7.5 Hz, 1H); 7.32 (dd, 7.8 and 0.9 Hz, 1H), 4.30-4.26 (m, 2H); 3.76-3.68 (m, 1H); 2.91-2.79 (m, 2H); 1.90-1.86 (m, 2H); 1.71-1.60 (m, 2H); 1.51 (s, 9H).

The following examples describe how 2-(1-(tert-butoxycarbonyl)piperidine-4-yl)benzoic acid (I) can be used to prepare ampreloxetine (or 4-[2-(2,4,6-trifluoro-phenoxymethyl)phenyl]piperidine) and salts thereof.

Example 7

Preparation of 4-(2-Hydroxymethylphenyl)piperidine-1-carboxylic Acid tert-Butyl Ester 2-(1-(tert-Butoxycarbonyl)piperidine-4-yl)benzoic acid (I) (5.0 g, 16 mmol, 1.0 eq.) and THF (130 mL, 1.7 mol) were combined at room temperature under nitrogen. Borane dimethyl sulfide complex (2.9 mL, 33 mmol, 2.0 eq.) was added dropwise and the mixture was stirred for 5 minutes, then heated at reflux for 1 hour. The mixture was cooled to room temperature and the reaction was quenched by adding MeOH (40 mL) dropwise. The mixture was then concentrated by rotary evaporation and the resulting material was azeotroped with MeOH (2×40 mL). The mixture was then diluted with EtOAc (100 mL), and washed with aqueous hydrochloric acid solution (1 M; 2×50 mL), then aqueous saturated sodium bicarbonate solution (2×50 mL), then saturated aqueous sodium chloride solution (1×50 mL). The organic layer was dried over anhydrous sodium sulfate, filtered, and concentrated in vacuo to yield 4-(2-hydroxymethylphenyl)-piperidine-1-carboxylic acid t-butyl ester (4.8 g) as a clear, light yellow oil that solidified upon sitting.

$^{1}$H NMR (CDCl$_3$) δ (ppm) 7.34-7.22 (m, 3H); 7.19 (dt, J=1.6 Hz, 7.2, 1H); 4.73 (s, 2H); 4.32-4.14 (m, 2H); 3.00 (tt, J=4.0 Hz, 12.0, 1H); 2.80 (t, J=11.6 Hz, 2H); 1.78-1.56 (m, 4H); 1.47 (m, 9H).

Example 8

Preparation of 4-[2-(Toluene-4-sulfonyloxymethyl) phenyl]piperidine-1-carboxylic Acid tert-Butyl Ester 4-(2-Hydroxymethylphenyl)piperidine-1-carboxylic acid t-butyl ester (0.4 g, 1.0 mmol, 1.0 eq.) and triethylenediamine (220 mg, 2.0 mmol, 1.4 eq.) were dissolved in DCM (11 mL, 170 mmol). The mixture was cooled at 0° C. under nitrogen and p-toluenesulfonyl chloride (290 mg, 1.5 mmol, 1.1 eq.) was added. The resulting mixture was stirred at 0° C. for 60 minutes. The mixture was diluted with EtOAc (50 mL) and washed with water (2×25 mL). The organic layer was dried over sodium sulfate, filtered and concentrated by rotary evaporation to yield the title compound (500 mg), which was used without further purification.

$^{1}$H NMR (CDCl$_3$) δ (ppm) 7.81 (t, J=2.0 Hz, 1H); 7.79 (t, J=2.0 Hz, 1H); 7.37-7.32 (m, 4H); 7.25-7.21 (m, 1H); 7.21-7.13 (m, 1H); 5.12 (s, 2H); 4.34-4.12 (m, 2H); 2.81-2.61 (m, 3H); 2.45 (s, 3H); 1.70-1.52 (m, 4H); 1.48 (s, 9H).

Example 9

Preparation of 4-[2-(2,4,6-Trifluorophenoxymethyl) phenyl]piperidine Trifluroacetic Acid Salt 4-[2-(Toluene-4-sulfonyloxymethyl)phenyl]piperidine-1-carboxylic acid tert-butyl ester (2.1 g, 4.7 mmol, 1.0 eq.) was dissolved in MeCN (46 mL, 890 mmol) and added to potassium carbonate (1.9 g, 14 mmol, 3.0 eq.) and 2,4,6-trifluorophenol (1.0 g, 7.0 mmol, 1.5 eq.). The mixture was shaken at 50° C. overnight, then cooled to room temperature. The supernatant was separated from the potassium carbonate and other solids. TFA (7 mL, 90 mmol, 20.0 eq.) was added to the supernatant and the mixture was shaken overnight at room temperature. The solution was then concentrated and the residue was dissolved in 1:1 acetic acid/water (5.0 mL). Additional acetic acid (2.0 mL) was added and the mixture was filtered and purified by preparative HPLC to yield the title compound (1.3 g, 97.5% purity). MS m/z: [M+H]$^+$ calcd for C$_{18}$H$_{18}$F$_3$NO, 322.13; found 322.2.

$^{1}$H NMR (CDCl$_3$) δ (ppm) 9.83 (br.s, 1H); 9.32 (br.s, 1H); 7.46-7.39 (m, 2H); 7.32 (d, J=6.8 Hz, 1H); 7.26-7.21 (m, 1H); 6.76-6.66 (m, 2H); 5.07 (s, 2H); 3.69-3.50 (m, 2H); 3.38 (t, J=11.6 Hz, 1H); 3.20-3.02 (m, 2H); 2.19 (q, J=12.8 Hz, 2H); 2.12-2.01 (m, 2H).

Example 10

Preparation of 4-(2-Hydroxymethylphenyl)piperidine-1-carboxylic Acid tert-Butyl Ester 4-(2-Carboxyphenyl)piperidine-1-carboxylic acid tert-butyl ester (5.0 g, 160 mmol, 1.0 eq.) and THF (100 mL, 1.0 mol) were combined at room temperature under nitrogen. Borane-THF complex in THF (1.0 M, 32.7 mL, 32.7 mmol, 2.0 eq.) was added dropwise over 10 minutes (5° C. exotherm, gas evolution). The reaction mixture was stirred at room temperature for 5 minutes, then heated at 50° C. for 1 hour. The reaction mixture was cooled to room temperature and the reaction was quenched by slowly adding MeOH (30 mL) (mild exotherm, significant gas evolution). The mixture was then concentrated by rotary evaporation. The resulting material was azeotroped with MeOH (2×50 mL). The crude product was dissolved in EtOAc (100 mL) and washed with saturated aqueous sodium bicarbonate solution (50 mL) and then saturated aqueous sodium chloride solution (50 mL). The organic layer was dried over anhydrous sodium sulfate, filtered, and concentrated in vacuo to yield 4-(2-hydroxymethylphenyl)piperidine-1-carboxylic acid tert-butyl ester (4.4 g) as a clear, light yellow oil that solidified upon sitting.

Example 11

Preparation of 4-(2-Methanesulfonyloxymethylphenyl)piperidine-1-carboxylic Acid tert-Butyl Ester 4-(2-Hydroxymethylphenyl)piperidine-1-carboxylic acid tert-butyl ester (50.0 g, 172 mmol, 1.0 eq.) was dissolved in DCM (500 mL, 8000 mmol). The mixture was cooled at 0° C. under nitrogen and methanesulfonic anhydride (44.8 g, 257 mmol, 1.5 eq.) was added in one portion. Diisopropylethylamine (47.8 mL, 274 mmol, 1.6 eq.) was added dropwise over 5 minutes and the mixture was stirred at 0° C. for 90 minutes. Water (400 mL, 20 mol) was added and the mixture was stirred for 5 minutes. The phases were separated, and the organic layer was washed with water (300 mL), dried over anhydrous sodium sulfate, and the solvent removed to yield the title compound (70 g) as a thick oil, which was used without further purification.

$^{1}$H NMR (400 MHz, DMSO-d$_6$) δ (ppm) 7.37-7.43 (m, 3H), 7.31 (d, 1H), 7.22 (m, 2H), 5.38 (s, 2H), 4.28 (m, 2H), 2.92-3.10 (m, 1H), 2.92 (s, 3H), 2.80-2.92 (m, 2H), 1.63-1.81 (m, 4H), 1.51 (s, 9H).

Example 12

Preparation of 4-[2-(2,4,6-Trifluorophenoxymethyl) phenyl]piperidine-1-carboxylic Acid tert-Butyl Ester 4-(2-Methanesulfonyloxymethylphenyl)piperidine-1-carboxylic acid tert-butyl ester (27.0 g, 60.6 mmol, 1.0 eq.) was dissolved in MeCN (540 mL) and added to potassium carbonate (25 g, 180 mmol, 3.0 eq.) and 2,4,6-trifluorophenol (13.5 g, 90.9 mmol, 1.5 eq.). The mixture was stirred vigorously at 50° C. for 6 hours, removed from the heat, and stirred overnight. The mixture was cooled at room temperature and diluted with EtOAc (700 mL) and water (700 mL). The phases were separated and the organic layer was washed with aqueous sodium hydroxide solution (1.0 M; 2×400 mL) and saturated aqueous sodium chloride solution (1×400 mL), and then dried over anhydrous sodium sulfate. The solvent was then removed to yield crude 4-[2-(2,4,6-trifluorophenoxymethyl)phenyl]piperidine-1-carboxylic acid tert-butyl ester (25.0 g). The crude product was combined with smaller scale runs for a total of 30 g and purified by chromatography (0-10% EtOAc in hexanes) to yield 4-[2-(2,4,6-trifluorophenoxymethyl)phenyl]piperidine-1-carboxylic acid tert-butyl ester (22.0 g).

Example 13

Preparation of 4-[2-(2,4,6-Trifluorophenoxmethyl)phenyl]piperidine Hydrochloride 4-[2-(2,4,6-Trifluorophenoxymethyl)phenyl]piperidine-1-carboxylic acid tert-butyl ester (22.0 g, 31.3 mmol, 1.0 eq.) was combined with 1.25 M HCl in EtOH (250 mL, 310 mmol, 10.0 eq.). The mixture was stirred at room temperature for 8 hours, then stored at −10° C. for approximately 48 hours. Most of solvent was removed by rotary evaporation. To the resulting thick slurry was added EtOAc (80 mL), followed by stirring at room temperature for 2 hours. A first crop of crystals was isolated by filtration, and the filter cake was washed with EtOAc (20 mL) and dried to yield the title compound (8.5 g, >99% purity) as a white solid. HPLC of the filtrate shows ~25% area of product. For the second crop, the solvent was removed by rotary evaporation and the resulting solid (~10 g) was slurried in EtOAc (40 mL), first at room temperature, then at 60° C., and again at room temperature to yield the title compound as a hydrochloride salt (1.7 g, >99% purity).

Two lots of the hydrochloride salt (18.5 g, 51.7 mmol) were combined with EtOAc (75 mL, 770 mmol). The resulting thick but free-flowing slurry was heated at 65° C. for 30 minutes, cooled to room temperature, and filtered. The flask and the filter cake were washed with EtOAc (20 mL), and the solids dried under high vacuum at room temperature overnight to yield the crystalline hydrochloride salt (18.2 g, 99.3% purity).

Example 14

Preparation of 4-[2-(2,4,6-Trifluorophenoxymethyl)phenyl]piperidine Hydrochloride Acetyl chloride (83.5 mL, 1170 mmol) was slowly added to EtOH (140 mL, 2.4 mol). 4-[2-(2,4,6-Trifluorophenoxymethyl)phenyl]piperidine-1-carboxylic acid tert-butyl ester (55.0 g, 117 mmol) dissolved in EtOH (100 mL, 2.0 mol) was added and the resulting mixture was stirred at room temperature for 6 hours. Most of solvent was removed by rotary evaporation. To the resulting thick slurry was added EtOAc (300 mL), followed by partial solvent removal to ~100 mL. EtOAc (200 mL) was added and the resulting slurry was stirred for 1 hour, filtered and dried to yield the title compound (28.0 g, ~99% purity). The filtrate was concentrated to a thick paste and IPAc (100 mL) was added, stirred for 1 hour, filtered and dried to further yield 5.0 g of the hydrochloride salt (~99% purity).

Two lots of the hydrochloride salt (83.0 g, 230 mmol, ~99% purity) were combined with EtOAc (250 mL, 2.6 mol). The resulting slurry was heated at 70° C. and then slowly cooled to room temperature, followed by stirring overnight. The resulting free-flowing slurry was filtered and the filter cake was washed with EtOAc (50 mL) then dried under high vacuum for approximately 48 hours to yield the crystalline hydrochloride salt (81.0 g, >99% purity).

The crystalline hydrochloride salt (50.0 g, 1.40 mol, >99% purity) was dissolved in IPA (250 mL, 3.3 mol), and the resulting slurry was heated to 75° C. Water (25 mL, 1.4 mol) was added. Complete dissolution was observed in 5 minutes, and the internal temperature of the solution was 65° C. The solution was slowly cooled to room temperature and then stirred at room temperature overnight. The resulting solids were filtered and dried under air for 2 hours to yield a semi-dry product. The solids were then dried under high vacuum at room temperature for approximately 48 hours to yield the title crystalline hydrochloride salt (44.1 g, 99.5% purity).

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A process for preparing a compound of formula I:

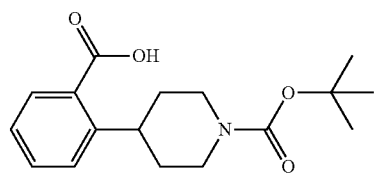

the process comprising:
(a) reacting a compound of formula 1:

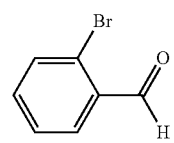

with a $C_{1-6}$ alkyl 3-oxobutanoate in the presence of piperidine to form a compound of formula 2:

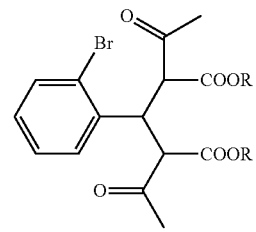

wherein each R is independently selected from $C_{1-6}$ alkyl;

(b) reacting the compound of formula 2 with an alkali metal hydroxide to form, after acidification of the reaction product with an acid, a compound of formula 3:

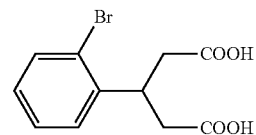

(c) reacting the compound of formula 3 with an ammonia reagent to form a compound of formula 4:

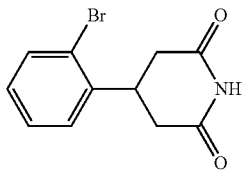

(d) reacting the compound of formula 4 with a reducing agent to form a compound of formula 5 or a salt thereof:

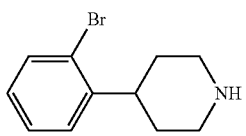

(e) reacting the compound of formula 5 or a salt thereof with di-tert-butyl dicarbonate to form a compound of formula 6:

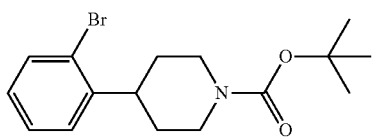

(f) reacting the compound of formula 6 with an alkyl lithium reagent to form a compound of formula 7:

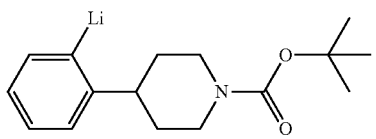

(g) reacting the compound of formula 7 with carbon dioxide to form the compound of formula I.

2. The process of claim 1, wherein each R group is independently selected from methyl and ethyl.

3. The process of claim 1, wherein both R groups are methyl.

4. The process of claim 1, wherein both R groups are ethyl.

5. The process of claim 1, wherein the alkali metal hydroxide is lithium hydroxide, sodium hydroxide or potassium hydroxide.

6. The process of claim 5, wherein the alkali metal hydroxide is potassium hydroxide.

7. The process of claim 1, wherein the acid is hydrochloric acid, hydrobromic acid, sulfuric acid, phosphoric acid or acetic acid.

8. The process of claim 7, wherein the acid is hydrochloric acid.

9. The process of claim 1, wherein the ammonia reagent is ammonia, urea, ammonium hydroxide, ammonium chloride or magnesium nitride.

10. The process of claim 9, wherein the ammonia reagent is urea.

11. The process of claim 1, wherein the reducing agent is sodium borohydride/boron trifluoride tetrahydrofuran complex or lithium aluminum hydride.

12. The process of claim 11, wherein the reducing agent is sodium borohydride/boron trifluoride tetrahydrofuran complex.

13. The process of claim 1, wherein the alkyl lithium reagent is n-butyl lithium or tert-butyl lithium.

14. The process of claim 13, wherein the alkyl lithium reagent is n-butyl lithium.

15. The process of claim 1, wherein the alkali metal hydroxide is potassium hydroxide; the acid is hydrochloric acid; the ammonia reagent is urea; the reducing agent is sodium borohydride/boron trifluoride tetrahydrofuran complex; and the alkyl lithium reagent is n-butyl lithium.

16. A process for preparing a compound of formula I:

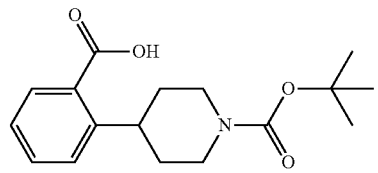

the process comprising:

(a) reacting a compound of formula 1:

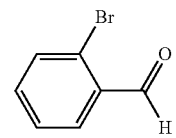

with ethyl 3-oxobutanoate in the presence of piperidine to form a compound of formula 2a:

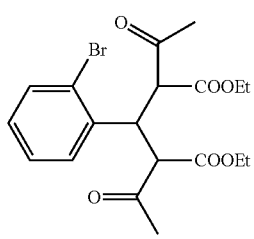

(b) reacting the compound of formula 2a with an potassium hydroxide to form, after acidification of the reaction product with hydrochloric acid, a compound of formula 3:

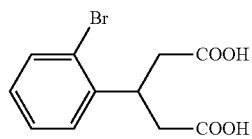

(c) reacting the compound of formula 3 with urea to form a compound of formula 4:

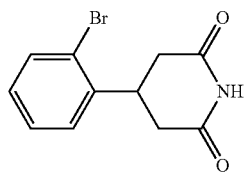

(d) reacting the compound of formula 4 with sodium borohydride/boron trifluoride tetrahydrofuran complex to form a compound of formula 5 or a salt thereof:

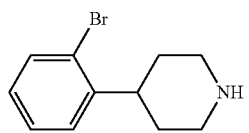

(e) reacting the compound of formula 5 or a salt thereof with di-tert-butyl dicarbonate to form a compound of formula 6:

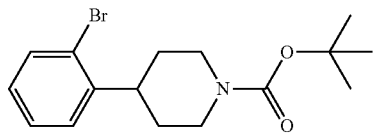

(f) reacting the compound of formula 6 with n-butyl lithium to form a compound of formula 7:

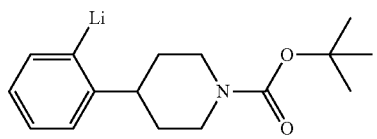

(g) reacting the compound of formula 7 with carbon dioxide to form the compound of formula I.

17. The process of claim 16, wherein step (d) and step (e) are conducted in the same reaction mixture without isolation of the product of step (d).

* * * * *